(12) United States Patent
Miller

(10) Patent No.: US 7,282,032 B2
(45) Date of Patent: Oct. 16, 2007

(54) PORTABLE RESPIRATORY DIAGNOSTIC DEVICE

(76) Inventor: Thomas P. Miller, 3123 Uplands, SE., Grand Rapids, MI (US) 49506

( * ) Notice: Subject to any disclaimer, the term of this patent is extended or adjusted under 35 U.S.C. 154(b) by 510 days.

(21) Appl. No.: 10/453,801

(22) Filed: Jun. 3, 2003

(65) Prior Publication Data

US 2004/0249300 A1    Dec. 9, 2004

(51) Int. Cl.
*A61B 5/00* (2006.01)
(52) U.S. Cl. ...................... 600/538; 600/533
(58) Field of Classification Search ............. 600/499; 128/204.21–204.24
See application file for complete search history.

(56) References Cited

U.S. PATENT DOCUMENTS

| | | | |
|---|---|---|---|
| 3,977,394 A * | 8/1976 | Jones et al. ............... 600/541 |
| 4,220,161 A | 9/1980 | Berlin et al. |
| 4,259,967 A | 4/1981 | Vooren et al. |
| 4,802,492 A | 2/1989 | Grunstein |
| 4,844,085 A * | 7/1989 | Gattinoni ................ 600/533 |
| 5,137,026 A | 8/1992 | Waterson et al. |
| 5,233,998 A | 8/1993 | Chowienczyk et al. |
| 5,261,397 A | 11/1993 | Grunstein |
| 5,379,650 A | 1/1995 | Kofoed et al. |
| 5,454,375 A | 10/1995 | Rothenberg |
| 5,501,231 A | 3/1996 | Kaish |
| 5,522,397 A | 6/1996 | Vermaak |
| 5,562,101 A | 10/1996 | Hankinson et al. |
| 5,720,709 A | 2/1998 | Schnall |
| 5,868,133 A * | 2/1999 | DeVries et al. ........ 128/204.21 |
| 5,875,777 A | 3/1999 | Eriksson |
| 5,924,994 A | 7/1999 | Harbrecht et al. |
| 6,019,731 A | 2/2000 | Harbrecht et al. |
| 6,066,101 A | 5/2000 | Johnson et al. |
| 6,068,602 A | 5/2000 | Tham et al. |
| 6,074,350 A | 6/2000 | Macklem et al. |
| 6,095,139 A * | 8/2000 | Psaros ................... 128/204.22 |
| 6,142,952 A | 11/2000 | Behbehani et al. |
| 6,179,784 B1 | 1/2001 | Daniels et al. |
| 6,183,423 B1 | 2/2001 | Gaumond et al. |
| 6,186,956 B1 | 2/2001 | McNamee |

(Continued)

FOREIGN PATENT DOCUMENTS

EP    1108391    6/2001

(Continued)

*Primary Examiner*—Robert L Nasser
(74) *Attorney, Agent, or Firm*—Warner Norcross & Judd LLP

(57) ABSTRACT

A portable, handheld device for measuring lung- and airway-specific respiratory parameters. The device defines a chamber in fluid communication with a mouthpiece. A sensor and/or a flow sensor monitor pressure and/or airflow within the device. A respiratory gas source, e.g., an internal pump, or an external compressor, is also in fluid communication with the chamber and a mouthpiece. The device operates in an active phase and a passive phase. In the active phase, a subject forcibly exhales into the device and the sensors collect spirometric data. In the passive phase, the pump is activated to pump air from the device and inflate the subject's lungs to a specific capacity. The sensors monitor pressure and/or flow as the air is introduced into the subject's respiratory system. The data collected by the sensor is used to determine lung and airway specific parameters, including but not limited to, airway conductance, airway resistance, airway compliance and total lung capacity.

10 Claims, 3 Drawing Sheets

U.S. PATENT DOCUMENTS

| | | |
|---|---|---|
| 6,203,502 B1 | 3/2001 | Hilgendorf et al. |
| 6,224,560 B1 | 5/2001 | Gazula et al. |
| 6,257,234 B1 | 7/2001 | Sun |
| 6,302,851 B1 | 10/2001 | Gedeon |
| 2003/0010339 A1 | 1/2003 | Banner et al. |

FOREIGN PATENT DOCUMENTS

| | | |
|---|---|---|
| WO | WO 89/10768 | 11/1989 |
| WO | WO 96/11717 | 4/1996 |

* cited by examiner

PORTABLE RESPIRATORY DIAGNOSTIC DEVICE

BACKGROUND OF THE INVENTION

The present invention relates to medical diagnostic devices, more particularly to devices that measure respiratory parameters.

It is often desirable to measure respiratory parameters to monitor and diagnose the progression of respiratory diseases and to make beneficial therapeutic recommendations. It is also desirable to measure respiratory parameters in individuals who have been exposed to smoke, biological or chemical substances, and to determine and prescribe appropriate treatment.

Respiratory parameters are based on a subject's ability to inhale or exhale. A subject's ability to produce airflow or pressure differentials, and thereby create measurable respiratory parameters, is significantly influenced and controlled by the subject's entire respiratory system, that is, the subject's chest wall musculature, diaphragm, lung parenchymal tissue and airway structure. Accordingly, it is difficult to measure respiratory parameters as they relate to specific organs or parts of organs, for example, the lungs or the airways. As a result, most attempted measurements of lung- or airway-specific respiratory parameters, for example, airway resistance ($R_{aw}$), airway conductance ($C_{aw}$), lung compliance, and total lung capacity (TLC) are at times inaccurate and do not reflect the actual lung and/or airway performance of the subject. Sometimes this inaccurate measurement may lead to misdiagnosis, or the prescription of unnecessary or harmful drugs or therapy.

Several devices are presently used to measure respiratory parameters of subjects, however, each device is based on airflow and pressure differentials generated by the entire respiratory system, and therefore are not lung- or airway-specific. One such device is a spirometer. A spirometer measures airflow rates and air volumes with a sensor as subject inhales or exhales through a mouthpiece on the spirometer. Another respiratory measurement device is the plethysmograph, which specifically measures respiratory parameters of airway resistance and airway conductance. The plethysmograph includes a large chamber in which a subject is enclosed. In operation, the subject pants within the chamber to create pressure changes in the chamber. The pressure changes are correlated to airflow changes within the subject's respiratory system to calculate $R_{aw}$ and $C_{aw}$ using an application of Boyle's law ($P_1 V_1 = P_2 V_2$). In addition to being space prohibitive due to its large, typically immobile chamber, like the spirometer, the plethysmograph is not lung- or airway-specific because the pressure and airflow changes inside the chamber are created by the subject's entire respiratory system.

A third device that measures respiratory parameters is included in a hospital-grade ventilator. U.S. Pat. No. 6,257,234 to Sun discloses this device, which superimposes a momentary sinusoidal pressure oscillation on the air pressure provided by the ventilator to the subject as the ventilator supports inspiration by the subject. The momentary sinusoidal pressure oscillation is evaluated to determine and calculate airway resistance. Although Sun may be used to measure airway resistance, it suffers several shortcomings. First, it is only effective for evaluating respiratory resistance in a ventilated subject. Second, if the forced impulse oscillation is introduced at the wrong time during inspiration, the collected data may be inaccurate. Further, the forced impulse oscillation provides only an instantaneous measurement of the subject's respiratory system, which may be inaccurate due to chest wall musculature fatigue or contraction, or the state of the lung parenchymal tissue at that specific moment the oscillation is imposed.

SUMMARY OF THE INVENTION

The aforementioned problems are overcome in the present invention which provides a portable respiratory monitoring device that includes a respiratory gas source that inflates the lungs of a subject to a pre-selected pressure and/or volume. The portable device includes pressure and/or flow sensors that monitor the pressure and/or flow as the device inflates the subject's lungs in a passive mode. The data collected by the sensors is then manipulated to calculate lung- or an airway-specific parameters including but not limited airway resistance, airway conductance, lung compliance and total lung capacity.

In one embodiment, the portable respiratory device is a hand-held unit including a pump that passively inflates the subject's respiratory system in a passive mode. Sensors within the unit monitor pressure and/or flow as a respiratory gas is introduced into a subject's respiratory system.

In another embodiment, the same device operates in an active mode, wherein a subject forcibly exhales through the device and the device simultaneously collects spirometric data.

The present invention is also directed to a method monitoring the respiratory system function of a subject generally including the steps of: prompting the subject to forcibly exhale; introducing a respiratory gas to fill the respiratory system a pre-selected amount; measuring at least one of a pressure and a flow of the respiratory gas introduced in the subject's respiratory system; and processing at least one of the pressure and flow to determine a respiratory system function parameter.

The portable diagnostic device of the present invention provides a simple and extremely portable monitoring apparatus that may be used in virtually any environment setting. The device readily may be used outside a clinic or hospital to provide on-the-scene respiratory parameter measurements in persons who have suffered smoke, biological or chemical substance exposure, and rapidly ascertain a treatment. Moreover because the portable diagnostic device of the present invention inflates a subject's respiratory system and/or airways, more reliable and accurate measurements of lung- and/or airway-specific parameters may be measured without the influence of other portions of the patient's respiratory system, for example, chest wall musculature, the diaphragm, lung parenchymal tissue and airway structure. Accordingly, extremely accurate measurements may be acquired with the device.

These and other objects, advantages and features of the invention will be more readily understood and appreciated by reference to the detailed description of the invention and the drawings.

DETAILED DESCRIPTION OF THE INVENTION

I. Overview

Figure 1:
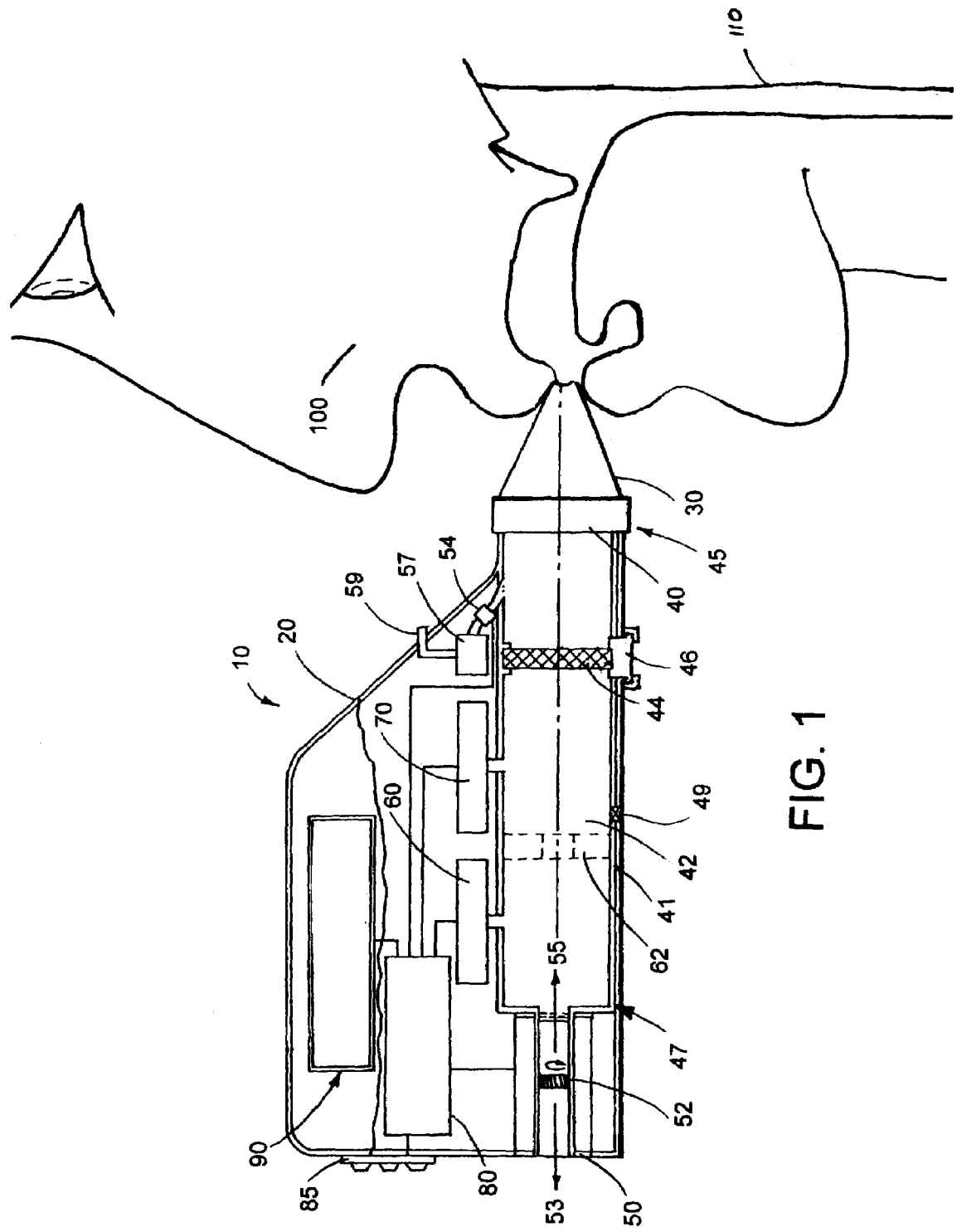
FIG. 1 is a broken side elevational view of the respiratory monitoring device of the present invention.

The portable respiratory monitoring device of the present invention is illustrated in FIG. 1 and generally designated 10. As shown, the portable device 10 includes a housing 20 within which components, including a tube 41, a pump 50, a flow sensor 70, pressure sensor 60 and a processor 80 are housed or contained. Optionally, the housing includes a keypad 85 to control the operation of the various components. A display 90 may be further joined with or disposed within the housing 20 to output data collected by the device 10. A mouthpiece 30, or optionally a mask (not shown), is releasably secured to the device and adapted to be inserted into the mouth of a subject 100 or over the nose and mouth of a subject, respectively.

In operation, the device operates in two primary modes or phases; an active mode and a passive mode. In the active mode, the pump 50 acts as a valve so that air may travel therethrough in direction 53, and/or direction 55, as shown. The subject 100 is instructed to perform normal tidal breathing through the mouthpiece 30, and thus the device 10, for several breaths. After maximal inspiration, the subject 100 is then prompted to forcibly exhale through the device. During expiration, the device collects spirometric data by monitoring the pressure and/or flow through the chamber 42 with sensors 60 and 70. In the passive mode, the pump 50 pump respiratory gas, such as oxygen, air, or the like in direction 55 through the chamber and thus into the respiratory system 110 of the subject 100. The pump continues pumping gas through the chamber and into the subject's respiratory system 110 until a desired capacity of the respiratory system, is reached. During the pumping, the pressure and flow within the chamber is monitored with sensors 60 and 70. The collected pressure and flow data is processed to calculate and output respiratory parameters of the respiratory system 110, for example, airway resistance ($R_{aw}$), airway conductance ($C_{aw}$), lung compliance, and total lung capacity (TLC), on the display 90.

II. Construction

The construction of the portable respiratory monitoring device of the present invention will now be described in detail with reference to FIG. 1. As shown, the housing is generally sized and shaped so that it can be held comfortably in one hand and held-up to a subject's mouth while measuring respiratory parameters of the subject 100. The device may also be configured so that the subject 100 can comfortably hold the device and self monitor their respiratory parameters.

A control panel 85 including a keypad is connected to or integrated with the housing 20. The keypad may include a start button, a selection button or other controls as desired to operate the device 10, collect data or output data. A display 90 is connected to or integral with the housing 20 to generate output as described in more detail below. The display 90 may be any conventional display, for example, a liquid crystal display. Moreover, as desired, the display 90 may be touch sensitive and a separate control panel may be eliminated.

A tube 41 is disposed in the housing. The tube defines a chamber 42. The tube may be of any cross section, but as shown, is a circular or elliptical. The tube includes a first end 45 and a second end 47. At the first end, an exit port 40 is defined. At the second end 47, the chamber 42 is in fluid communication with a pump 50.

At the exit port 40, a mouthpiece 30 is releasably secured to the device 10, preferably to the housing 20. The mouthpiece is preferably disposable or easily cleaned and disinfected to prevent transmission of pathogens from one subject to the next. The mouth piece may include a feature that mates with the housing to join the mouthpiece in the housing. Optionally, the mouthpiece 30 may be substituted with a mask (not shown) that fits over the subject's mouth and/or nose.

In communication with the chamber and/or mouthpiece is an optional safety release valve 49. This release valve may be constructed to automatically relieve excess pressure beyond a pre-selected pressure to prevent harm to the subject.

Optionally, a filter 44 may be disposed in the tube 41 upstream of specific components to prevent contamination of these components. As shown, the filter 44 is disposed between the mouthpiece and the sensors 60 and 70. The housing 20 may include a filter access 46 to enable a user to access the filter 44 and replace it if necessary. In one embodiment, the filter is constructed of a porous material that is permeable to air but impermeable to liquids. Accordingly, saliva or other materials in air exhaled from a subject is prevented from contaminating the remainder of the chamber 42, for example, the pressure sensor 60 and/or flow sensor 70. In a specific embodiment, the filter is constructed of a hydrophobic filter media, such as 1¹⁄₁₆ inch thick hydrophobic polyethylene, the 10 micron pour size, and about a 50% porosity. Of course, other medias with different characteristics may be chosen for the application as desired. A suitable filter for the device 10 is a specially fitted Vitalograph® disposable bacterial/viral filter, available from Vitalograph, Inc. of Lenexa, Kans. As desired, the filter and related components may be absent from the device 10.

FIG. 1 also shows a flow source 50 in fluid communication with the chamber 42. The flow source 50 may be any pump, compressed gas supply, or mini-compressor, that can transfer air through the chamber, to a subject's respiratory system 110. As shown, the flow source is a pump that is disposed in the housing, however, the pump may be external or partially external to the housing as desired. The pump shown includes an internal turbine 52 that introduces respiratory gas, for example air, from the environment, into the chamber 42 and out the mouthpiece 30. Other respiratory gases, or other gases in general, may be used with the device as desired. Preferably, the flow 55 of respiratory gas produced by the pump is sufficient to inflate the lungs of the subject 100 to a pre-selected capacity. The pump 50 may be configured so that the turbine 52, or other component of the pump if a non-turbine type pump, does not interfere with the flow of air 53 when a subject exhales through the device 10.

With further reference to FIG. 1, the pressure sensor 60 and flow sensor 70 are in fluid communication with the chamber 42. The pressure sensor 60 is a conventional and/or miniaturized pressure measuring sensor. One example of such a sensor is a Samba 3000 pressure transducer, which is available from Linton Instrumentation of Norfolk, England. Other pressure measuring sensors may be used as the application requires. The flow sensor 70 may be conventional and/or miniaturized pneumotachometer. The flow sensor may also be a flow-interrupting, or occluding valve sensor, such as the sensor used in a MicroRint transducer, available from TriMed, Inc. of Miami, Fla. Optionally, a reducing orifice 62 or mesh screen (not shown) may be included in the chamber 42 to induce a pressure drop from one side to the other and assist the sensors in determining pressure and/or flow in the chamber 42. Optionally, one of the sensors 60 or 70 may be absent as the application requires.

The pressure sensor 60 and flow sensor 70 may be in communication with the processor 80 so that any flow or pressure measured by the sensors is transferred to the processor 80. The processor 80 may be in communication via electrical wiring or other communication means with the pressure sensor 60, or flow sensor 70. Where a display 90 is included in the device 10, the processor also may be in communication with the display.

The processor processes signals provided by the pressure sensor and/or flow sensor 60 and 70, and, optionally, includes a memory to store the pressure and/or flow information or data. The processor manipulates the data as described in further detail below to output respiratory parameters including, for example, but not limited to airway resistance, airway conductance, lung compliance, total lung capacity and/or other values determined by pressure-flow relationships or individual measurements of pressure and/or flow. The processor 80 may be further in communication with keypad 85 so that a user can input data, store data, or control the various components of the device 10 through the processor 80. Optionally, the processor performs these functions automatically without user input. Moreover, the processor may store instructions for operation of the device 10, and output these instructions to a user via the display.

As further shown in FIG. 1, the device 20 may include an optional reservoir 57. The reservoir 57 may be in fluid communication with the chamber 42, and include a filling port 59 to add material to the reservoir 57. In one embodiment, the reservoir stores medicaments, for example, bronchodilators or other therapeutic drugs. These drugs may be in a gaseous or liquid phase. The reservoir may further include a releasing device, for example, a small pump 54. This releasing device may also be any outlet that enables the material to be selectively released through the device to the subject 100. As shown, the pump 54 is in communication with the processor 80, which controls the pump 54 so that the medication stored within the reservoir 57 is introduced into the chamber 42 or otherwise dispensed from the device 10 in pre-selected amounts. Optionally, the pump may introduce the medication as the pump 50 introduces respiratory gas into the respiratory system 100. In this manner, the medication may be introduced into the respiratory system under pressure, thus allowing greater diffusion and/or deposition in the pressurized respiratory tract 110. The effect on relative airway resistance, compliance, conductance and total lung capacity before, during or after administration of the medication may also be monitored as described in further detail below.

III. Operation

The operation of the portable respiratory parameter measurement device of the present invention will now be described. In general, the device 10 is operable in at least one of an active mode and a passive mode. In the device shown, the active mode, also referred to as the spirometric mode, is initiated to take measurements via the keypad 85. Specifically, the pump 50 is deactivated via the keypad 85 to allow gas flow 53 through the pump. In embodiments where the pump allows gas to pass through it when it is powered, the pump need not be deactivated. The subject is then prompted, optionally by the display 90 or an attending physician or via instructions previously supplied to the subject, to begin normal tidal breathing. When the subject inspires, gas is drawn in direction 55 through the pump, the chamber, the filter (where applicable), the mouthpiece (where applicable) and into the subject's respiratory airways 110, which although not shown also include the subject's lungs, oropharynx, etc. During expiration, the gas flows in reverse direction 53 through the device out from the subject's airways 110. In one embodiment, this tidal breathing enables the user to become comfortable with the mouthpiece 30 or face mask (not shown) when used.

The subject is then prompted as above to take a deep breath, i.e., to inspire as much as possible, and then forcibly exhale as long and with as much force as their respiratory system will allow them. During this forced expiration, the flow sensor 70 and/or pressure sensor 60 measures the flow through and/or pressure in, respectively, the chamber 42. The flow and/or pressure sensor may be calibrated to sense the beginning of expiration and flow in direction 53 to begin the measuring process. The data collected by the flow and/or pressure sensor is transferred to the processor 80 and may be stored therein. In one embodiment, one or both of the sensors collect spirometric data including, but not limited to, forced vital capacity ("FVC"), forced expiratory volumes ("FEV") and expiratory flows ("FEF25-75, etc."). The processor 80 displays these measurements on the screen 90 so that the user may review the data. Calculation of the spirometric data is described in the article *Standardization of Spirometry, Respiratory Care*, Vol. 32, No. 11, pp. 1039-1060 (1987), which is hereby incorporated by reference. Other conventional methods may be used by the processor to calculate the spirometric data as desired. Optionally, the forced expiration may be repeated a pre-selected number of times to record different values. The highest values may then be used for later processing as desired.

With the active phase complete, the passive phase begins. Incidentally, the active phase or passive phase may be performed alone, without the other, as the application requires. In the passive phase, the subject is prompted to exhale, for example, by an attending physician or by the display 90 or as in previously supplied instructions, as much as possible and then to stop breathing. After the subject has exhaled, the subject stops breathing. The subject than allows the device 10 to "breath" for them by introducing a respiratory gas into their respiratory system 110. Typically, the respiratory gas is simply air pumped through the device, but may be any other gas as desired.

During the passive phase, the pump 50 pumps respiratory gas from the environment, or from a compressed gas source (FIG. 3) into the chamber 42, through the filter (where applicable), out the mouthpiece 30 (where applicable), and into the subject's respiratory system 110. Preferably, the subject is prompted or instructed to attempt to keep their chest muscles relaxed and therefore not assist the device for inspiration or expiration. Alternatively, gas flow could be generated from compressed air or air tank without a pump or compressor in fluid communication with the device.

In one embodiment, the pump 50 continues to operate, forcing respiratory gas in direction 55 into the respiratory system 110 of the subject until a pre-selected volume of air passing through the chamber 42, or pressure within the chamber 42, is detected by the flow sensor 70 and/or pressure sensor 60. The processor may then display an indicator or sound an alarm (not shown) to inform the subject that the passive phase is complete. The pump 50 may introduce a volume of respiratory gas into the respiratory system 110 of the subject equal to a volume of about 50%, more preferably about 70%, and even more preferably about 80% of the total lung capacity of the subject. This total lung capacity may be calculated as described in detail below.

Optionally, the amount of respiratory gas introduced in the respiratory system 110 by the pump 50 and/or the operation of the pump may be determined based on the spirometric data obtained during the active mode. For example, one may choose to introduce a respiratory gas corresponding to about 10%, about 25%, about 50%, about 75% or some other percentage of the total lung capacity. The choice to introduce variable volumes of air will be determined by which components of the pulmonary anatomy one is interested in targeting (i.e., different volumes will differentially affect the central, middle or distal airways). One may choose to follow pressure and flow valves corresponding to an entire range of volumes any value from 0 to 100% of total lung capacity at full volume.

As the pump 50 introduces respiratory gas into the respiratory system 110 of the subject 100, the pressure sensor 60 and/or flow sensor 70 senses and measures the pressure in and/or flow through the chamber 42, which is directly correlated to the pressure in and flow through the respiratory system 110 over time. Preferably, the measurements are continued throughout the entire passive mode.

The pressure and airflow measured by the sensors 60 and 70 may be recorded by the sensors or transferred to the processor for storage and data manipulation. This flow and/or pressure data within the chamber is indicative of the same parameters in the subject's respiratory system 110.

Figure 2A:
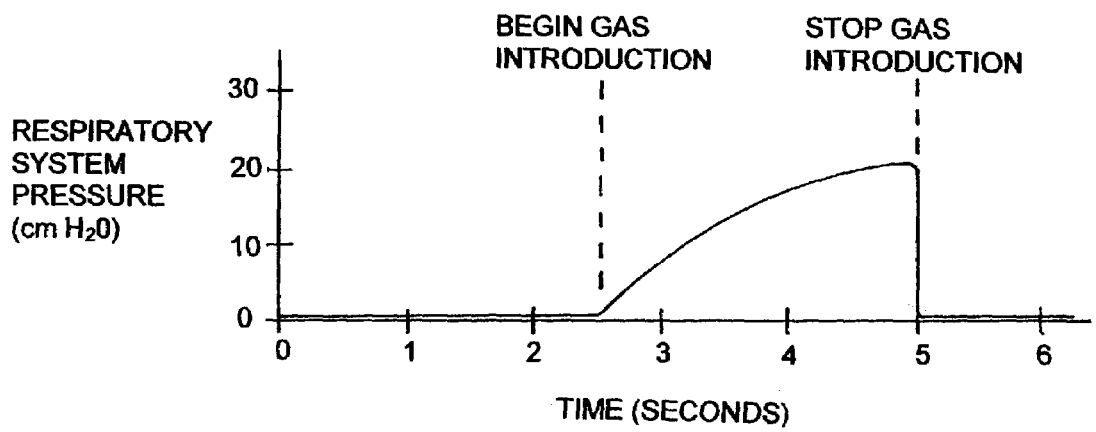
FIG. 2 is a graph illustrating measurements of respiratory volume, airflow and pressure that would be recorded using the portable device of the present invention.
Figure 2B:
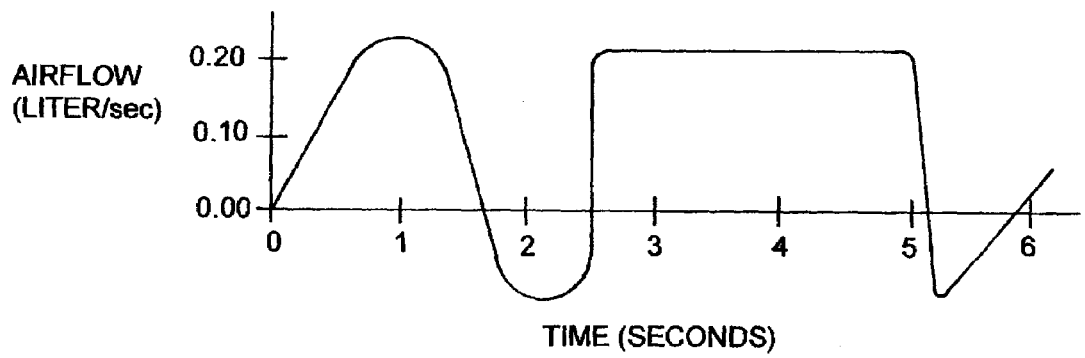
Figure 2C:
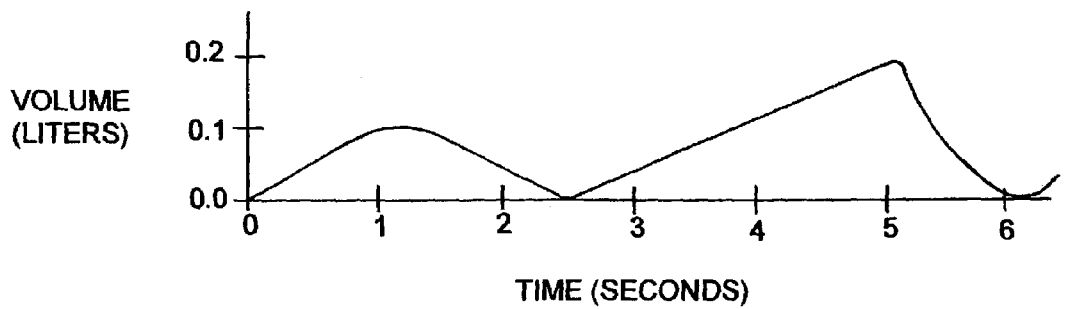

The graphs in FIGS. 2a-2c illustrate data that may be collected during the passive mode. The data in FIGS. 2a-2b is based on the pressure and flow sensed by the pressure sensor 60 and/or flow sensor 70. As shown, before the passive phase begins, i.e., before the respiratory gas is introduced by the pump 50 through the chamber 42, the airway pressure is relatively constant. As shown in FIGS. 2b and 2c, the airflow and volume of air vary according to normal tidal breathing. However, after the full expiration of the subject at time 2.5 seconds, the pump begins to introduce the respiratory gas into the respiratory system 110 of the subject. Thereafter, the pressure, shown in FIG. 2a, briefly fluctuates and then begins to steadily increase. Likewise, volume in FIG. 2c begins to increase as well. Airflow in FIG. 2b on the other hand, maintains a steady state due to the pump introducing respiratory gas into the respiratory system 110 of the subject 100 at a constant rate. After the passive mode ends, for example, at time 5 seconds, the pump 50 no longer introduces respiratory gas into the respiratory system. Accordingly, the pressure and airflow decreases substantially, along with the volume.

Depending on the amount of "noise" generated by the airflow and/or the speed at which the pressurized airflow sensors can acquire data, brief pauses in the airflow may be desired. The brief pauses may be implemented by briefly interrupting the flow generated by the flow source. Alternatively, the pauses may be implemented by a valve (not shown) disposed between the pump and the chamber and/or the sensors, which briefly closes to interrupt the airflow.

From the data collected by the sensors in the graphs in FIGS. 2a-2c, measurements of airway resistance, airway conductance, lung compliance and total lung capacity, may be computed as described below.

Total lung capacity (TLC), i.e., the total lung capacity in volume of a subject's lungs, may be calculated through linear regression using factors including the subject's age, height, weight, race and the change in slope of the pressure changes measured as the airflow and volume of respiratory gas introduced to the respiratory system of the subject approaches full volume capacity. Another method for calculating the total lung capacity implements Boyle's law, and uses the equation:

$$V_1 = P_2/P_1 V_2 - 1/V_2$$

Wherein $P_1$ is the pressure measured at the residual volume of the lungs (i.e., when the subject has fully exhaled), $V_1$ is the residual volume of the lungs, $P_2$ is the pressure after passive inflation of the lungs and $V_2$ is the volume added during passive inflation. Adding the residual volume $V_1$ plus the volume added during passive inflation $V_2$ yields the total lung capacity or volume.

Airway resistance ($R_{aw}$) is defined as the pressure change per unit flow as gas flows into or out of the lungs, and may be measured in centimeters $H_2O$ per liter per second. $R_{aw}$ can be calculated by dividing the slope of the pressure/volume curve by the slope of the flow/volume curve, which is computed using the following equation:

$$R_{aw} = \frac{\frac{\Delta P/\Delta t}{\Delta V/\Delta t}}{\frac{\Delta V/\Delta t}{\Delta V/\Delta t}}$$

The changes in volume and pressure in the above equation are determined from data gathered from the sensors and illustrated in the graphs of FIGS. 2a-2c.

Airway conductance $G_{aw}$ refers to the amount of flow generated per unit change in pressure across the respiratory airway, and is represented in units of liters per second per centimeter $H_2O$. $G_{aw}$ is also the reciprocal of airway resistance, i.e., $1/R_{aw}$.

Lung compliance refers to the distensibility of lungs in a subject. Dynamic compliance $C_{rs}$ of the respiratory system is typically defined by volume change per unit, pressure change in units of liters per centimeter $H_2O$. Compliance may be calculated by dividing the slope of the volume curve by the slope of the pressure curve according to the following equation:

$$C_{rs} = \frac{\Delta V \Delta t}{\Delta P/\Delta t}$$

Alternatively, lung compliance may be calculated using conventional equations implemented in mechanical ventilators, using the equation:

$$C_{rs} = \frac{V_d - (P_p - \text{PEEP})}{(P_p - \text{PEEP})}$$

Wherein $V_d$ is the volume of respiratory gas delivered, $P_p$ is the plateau pressure and PEEP is the positive end expiratory pressure in the patent after the passive phase. To measure $P_p$, the flow of air into the subject's lungs is stopped or occluded during inspiration. To generate this inspiratory hold, the flow source 50 may be paused or a valve (not shown) may be closed to stop or occlude flow. Other calculations using pressure and flow relationships may be used as desired for specific clinical and research applications.

IV. Alternative Embodiments

Figure 3:
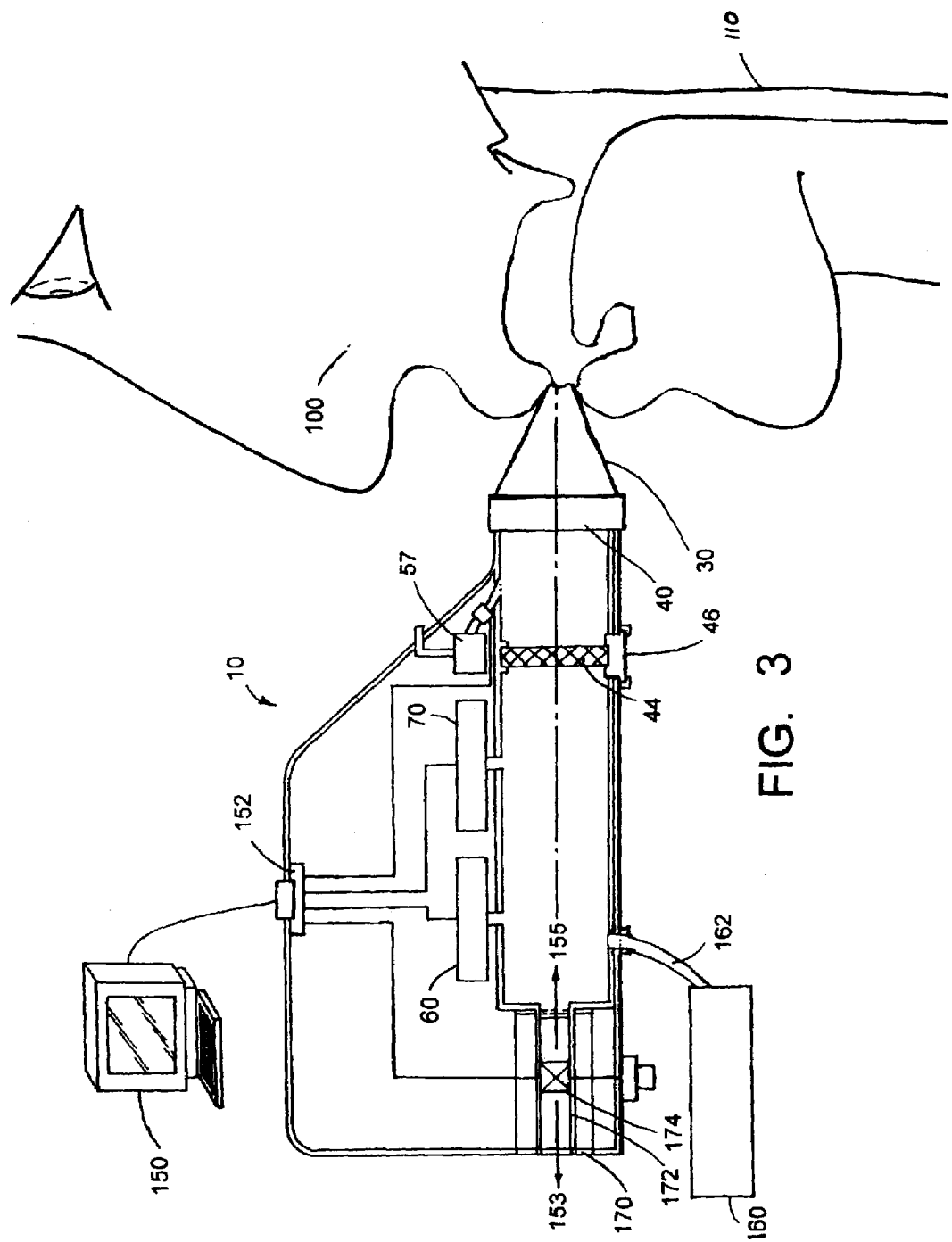
FIG. 3 is a broken side elevational view of an alternative embodiment of the respiratory monitoring device.

An alternative embodiment according to the present invention is shown in FIG. 3. This embodiment is substantially similar to the embodiment of FIG. 1, except that the device 10 is in communication with a computer 150 and pressure is supplied to the chamber 42 via a compressed air supply 160. As shown, the components of the device, i.e., the pressure sensor 60, the flow sensor 70 and the optional medicament dispenser 57 are in electrical communication with the port 152. The port which may be any conventional data port, e.g., a USB port, is in communication with communication line, which is further in communication with the computer. The computer 150 may function like the processor in the embodiment shown in FIG. 1 and monitor, calculate and display on the computer 150, the same parameters as the processor.

The compressor 160 may be a conventional processor in fluid communication via line 162 with the chamber 42. The compressor 160, although not shown, may also be in communication with the computer so that a user may operate the compressor with the computer. The device 10 in FIG. 3 also optionally includes a valve 172 operated by either the computer 150 or via the push button control 174 to allow airflow in either or both of the directions as indicated by the arrows 153 and 155. Preferably, the valve 174 closes in the passive phase so that respiratory gas flows into the chamber 42 out the mouthpiece and into the respiratory system 110 of the subject. Although not shown, the device may similarly be outfitted with a pressure safety valve as desired. The device 10 shown in FIG. 3 operates under the active phase and passive phase as described above except that in the passive phase, respiratory gas is introduced into the subject's respiratory system 110 via the compressor 160. Additionally, the computer 150 monitors and/or controls the sensors of the device.

Other applications of the device of the present invention include administering to a subject's respiratory system a known volume of gas measured by a sensor placed near the mouthpiece of the device or other location as desired. For example, carbon monoxide may be used and the carbon monoxide diffusing capacity calculated optionally by the processor. Further optionally, helium may be used and a total lung capacity derived by a conventional dilution technique. Such a techniques and calculations are described in the *Manual of Pulmonary Function Testing*, Ruppel G L., 7$^{th}$ Ed. (1998) which is incorporated by reference. Other types of gases may be administered to a subject and other useful information derived as desired.

The above descriptions are those of the preferred embodiments of the invention. Various alterations and changes can be made without departing from the spirit and broader aspects of the invention as defined in the appended claims, which are to be interpreted in accordance with the principles of patent law including the doctrine of equivalents. Any references to claim elements in the singular, for example, using the articles "a," "an," "the," or "said," is not to be construed as limiting the element to the singular.

The embodiments of the invention in which an exclusive property or privilege is claimed are defined as follows:

1. A self-contained diagnostic device for measuring a respiratory parameter of a subject having lungs with a capacity comprising:
   a portable housing including a tube defining a chamber;
   at least one of a mouthpiece and a mask releasably secured to said housing and in fluid communication with said chamber;
   at least one of an airflow sensor and a pressure sensor disposed in said housing in fluid communication with said chamber and adapted to measure at least one of airflow and pressure within the chamber;
   a pump disposed substantially entirely in said housing, said pump operated in an active mode and passive mode, said pump in said active mode enabling the subject to perform tidal breathing, said pump in said passive mode generating a gas flow of respiratory gas that travels through said chamber to the at least one of a mouthpiece and a face mask so that the respiratory gas inflates the lungs of the subject to a pre-selected portion of the capacity, said pump ceasing to provide the gas flow into the lungs after the respiratory gas inflates the lungs of the subject to the pre-selected portion of the capacity, said pump incapable of automatically sustaining continuous normal tidal breathing for the subject for multiple breaths in either of said active mode and said passive mode; and
   means for assisting in diagnosis of reduced pulmonary function resulting from at least one of smoke exposure, biological substance exposure, chemical substance exposure and a disease affecting the lungs of the subject.

2. The device of claim 1 comprising a processor in communication with said at least one of said flow sensor and said pressure sensor to collect at least one of volume data and flow data measured by the at least one of the flow sensor and the pressure sensor.

3. The device of claim 2 comprising a display coupled to the housing that outputs the at least one of the volume data and flow data.

4. The device of claim 2 wherein the processor processes the at least one of volume data and flow data and outputs at least one of airway resistance, airway conductance, lung compliance and total lung capacity to the display.

5. The device of claim 1 comprising a filter disposed in said housing adjacent the at least one of said flow sensor and said pressure sensor to prevent contamination of the at least one flow sensor and pressure sensor.

6. A portable diagnostic device for measuring respiratory parameters of a subject having lungs with a capacity comprising:
   a handheld housing;
   a chamber disposed in said housing;
   at least one of a pressure sensor and a flow sensor disposed in the housing in fluid communication with the chamber, said pressure sensor generating a pressure signal representative of pressure in the chamber, said flow sensor generating a flow signal representative of flow in the chamber;
   an output portion in fluid communication with the chamber;
   a flow source in fluid communication with the output portion, said flow source operating in at least one of a first mode wherein said flow source introduces no flow into the chamber, and a second mode wherein said flow source introduces a respiratory gas into the chamber so that said respiratory gas travels through said output portion to inflate the lungs of the subject from a first capacity to a second capacity, said flow source no longer introducing respiratory gas to the lungs of the subject after the second capacity is attained, said flow source incapable of automatically sustaining continuous normal tidal breathing of the subject for multiple breaths in either of the first or second modes; and
   a processor in communication with the at least one of the pressure sensor and the flow sensor to collect at least one of the pressure signal and the flow signal when said flow source is in at least one of said first mode and said second mode.

7. The portable device of claim 6 wherein the at least one of the pressure signal and flow signal includes at least one of forced vital capacity data, forced expiratory volume data and forced expiratory flow data.

8. The portable device of claim 6 wherein the flow source is a pump disposed substantially entirely in the housing.

9. The portable device of claim 6 comprising a display joined with the housing that displays the at least one of forced vital capacity data, forced expiratory volume data and forced expiratory flow data.

10. The portable device of claim 6 comprising a medicament reservoir, said medicament reservoir in fluid communication with at least one of said chamber and said output portion, said medicament reservoir introducing a medicament into the respiratory gas as the respiratory gas is introduced into the output portion so that the medicament is transported to the lungs of the subject in said passive mode.

* * * * *